(12) United States Patent
Farina et al.

(10) Patent No.: US 9,138,454 B2
(45) Date of Patent: Sep. 22, 2015

(54) TRANSFERRIN FOR USE IN THE TREATMENT AND/OR PROPHYLAXIS OF AUTOIMMUNE DISEASES

(75) Inventors: Claudio Farina, Pisa (IT); Ester Ascione, Santa Maria Capua Vetere (IT); Pierangelo Giovacchini, Lammari-Capannori (IT); Ferdinando Nicoletti, Cannizzaro-Acicastello (IT)

(73) Assignee: KEDRION S.P.A., Pascoli (IT)

( * ) Notice: Subject to any disclaimer, the term of this patent is extended or adjusted under 35 U.S.C. 154(b) by 0 days.

(21) Appl. No.: 13/574,646

(22) PCT Filed: Feb. 15, 2011

(86) PCT No.: PCT/IB2011/050623
§ 371 (c)(1),
(2), (4) Date: Jul. 23, 2012

(87) PCT Pub. No.: WO2011/098990
PCT Pub. Date: Aug. 18, 2011

(65) Prior Publication Data
US 2012/0296071 A1 Nov. 22, 2012

(30) Foreign Application Priority Data
Feb. 15, 2010 (IT) .................. FI2010A0020

(51) Int. Cl.
*A61K 38/40* (2006.01)
*C07K 14/79* (2006.01)
*A61K 38/01* (2006.01)

(52) U.S. Cl.
CPC .................. *A61K 38/017* (2013.01)

(58) Field of Classification Search
CPC .................. A61K 38/40; C07K 14/79
USPC ........................................ 530/394
See application file for complete search history.

(56) References Cited

U.S. PATENT DOCUMENTS

| 5,849,293 | A | 12/1998 | Vargas |
| 6,069,193 | A | 5/2000 | Vargas et al. |
| 6,126,955 | A | 10/2000 | Ardehali et al. |
| 6,255,278 | B1 | 7/2001 | Pierpaoli |
| 6,326,473 | B1 * | 12/2001 | Parkkinen et al. ............ 530/394 |
| 6,328,966 | B1 | 12/2001 | Pierpaoli |
| 2003/0229012 | A1 | 12/2003 | Thomas |
| 2010/0035992 | A1 * | 2/2010 | Bhushan et al. ............... 514/566 |

FOREIGN PATENT DOCUMENTS

| WO | WO 2007/076505 | * 12/2006 | ............. A61K 38/40 |
| WO | WO2008/142102 A3 | 11/2008 | |

OTHER PUBLICATIONS

Aamodt, G. et al. "The Association Between Water Supply and Inflammatory Bowel Disease Based on a 1990-1993 Cohort Study in Southeastern Norway" 2008 Am J Epidemiol 168 1065-1072.*
Andrews, F. et al "Effect of iron chelation on inflammatory joint disease" 1987 Annals of Rheumatic Diseases 46, 327-333.*
Khali, M. et al. "Iron and Neurodegeneration in Multiple Sclerosis" 2011 vol. 2011 Article ID 606807.*
Ascione, E. et al. "A simple method for large-scale purification of plasma derived apo-transferrin" 2010 Biotechnol. Appl. Biochem. 57, 87-95.*
Mangano et al. "The immunobiology of apotransferrin in type 1 diabetes" Clinical and experimental Immunology 2012 169: 244-252.*
Adamo et al.; "Remyelination After Cuprizone-Induced Demyelination in the Rat is Stimulated by Apotransferrin"; Experimental Neurology 198 (2006) 519-529.
Lesnikova M. et al.; "Upregulation of Interleukin-10 and Inhibition of Alloantigen Responses by Tranferrin and Transferrin-Derived Glycans"; J. Hematother Stem Cell Res.; Jun. 9, 2000 (3): 381-92. (Abstract-1 page).
Written Opinion of the International Searching Authority of International Application No. PCT/IB2011/050623 dated Aug. 15, 2012.
International Search Report for International Application No. PCT/IB2011/050623 dated May 11, 2011.

* cited by examiner

*Primary Examiner* — Karen Cochrane Carlson
(74) *Attorney, Agent, or Firm* — Abelman, Frayne & Schwab

(57) ABSTRACT

The present invention describes pharmaceutical compositions containing APOTf for use in preventing (or delaying the onset) and treating autoimmune diseases. Based on the experimental data obtained, the molecule has the surprising capacity to favorably modify the immune response profile both in vitro and in vivo.

11 Claims, 15 Drawing Sheets

FIG 3
A
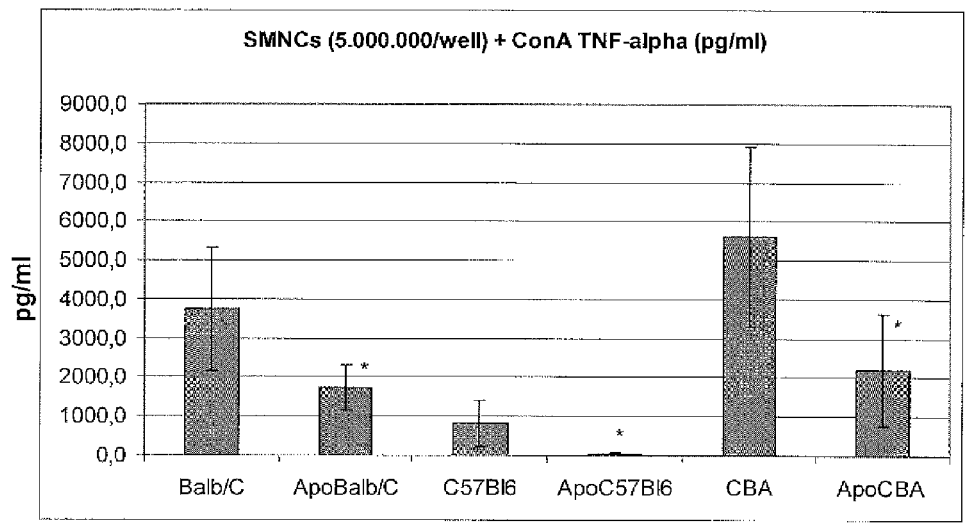
B
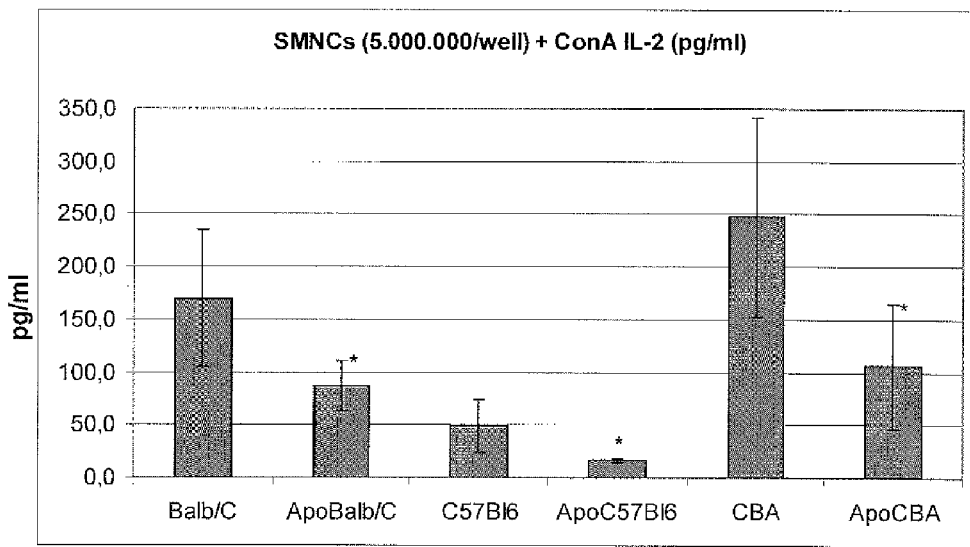

A

| PCs (1,000,000/well) + LPS IL-1β (pg/ml) | | | | | |
|---|---|---|---|---|---|
| Incubation | Strain | Dose | N° samples | Mean | S.D. |
| 5h | CBA | 0 | 6 | 285,3 | 72,9 |
| 5h | CBA | 12,5ugApo | 6 | 239,0 | 42,4 |
| 24h | CBA | 0 | 8 | 941,9 | 147,1 |
| 24h | CBA | 12,5ugApo | 8 | 934,7 | 133,0 |

B

| PCs (1,000,000/well) + LPS 24h TNF-α (pg/ml) | | | | |
|---|---|---|---|---|
| Strain | Dose | N° samples | Mean | S.D. |
| CBA | 0 | 10 | 1210,5 | 579,3 |
| CBA | 12,5ugApo | 10 | 1244,8 | 502,4 |

| PCs (5,000,000/well) 24h TNF-α (pg/ml) | | | | |
|---|---|---|---|---|
| Strain | Dose | N° samples | Mean | S.D. |
| Balb/C | 0 | 6 | 1294,49 | 425,42 |
| Balb/C | 12,5ugApo | 6 | 1321,63 | 231,65 |
| C57Bl6 | 0 | 2 | 2447,6 | 0 |
| C57Bl6 | 12,5ugApo | 6 | 2156,11 | 397,69 |

| PCs (5,000,000/well) + LPS 24h TNF-α (pg/ml) | | | | |
|---|---|---|---|---|
| Strain | Dose | N° samples | Mean | S.D. |
| Balb/C | 0 | 6 | 2186,12 | 163,74 |
| Balb/C | 12,5ugApo | 6 | 2098,96 | 334,4 |
| C57Bl6 | 0 | 6 | 2561,92 | 280,49 |
| C57Bl6 | 12,5ugApo | 6 | 2883,42 | 694,74 |

FIG 6
A
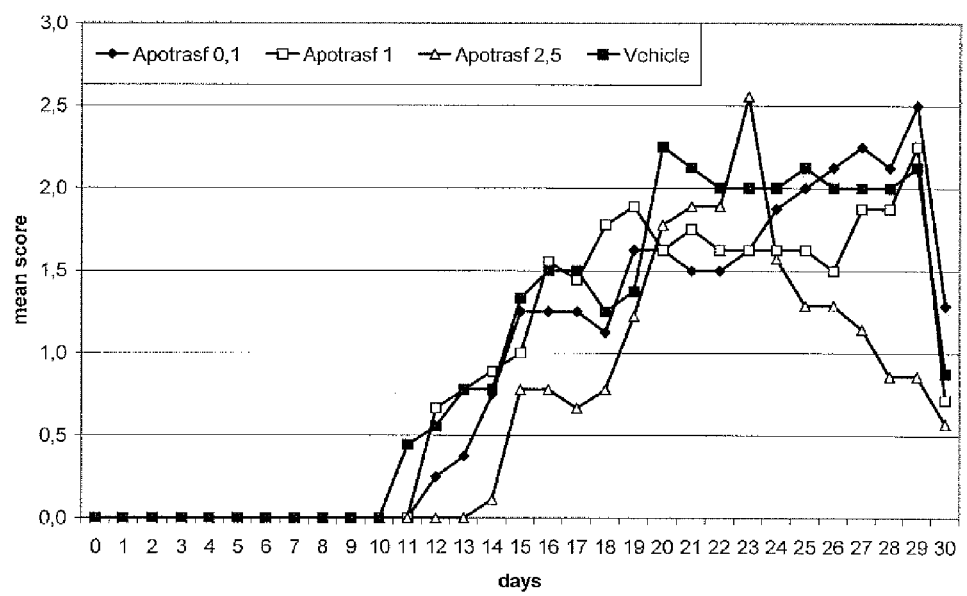
B
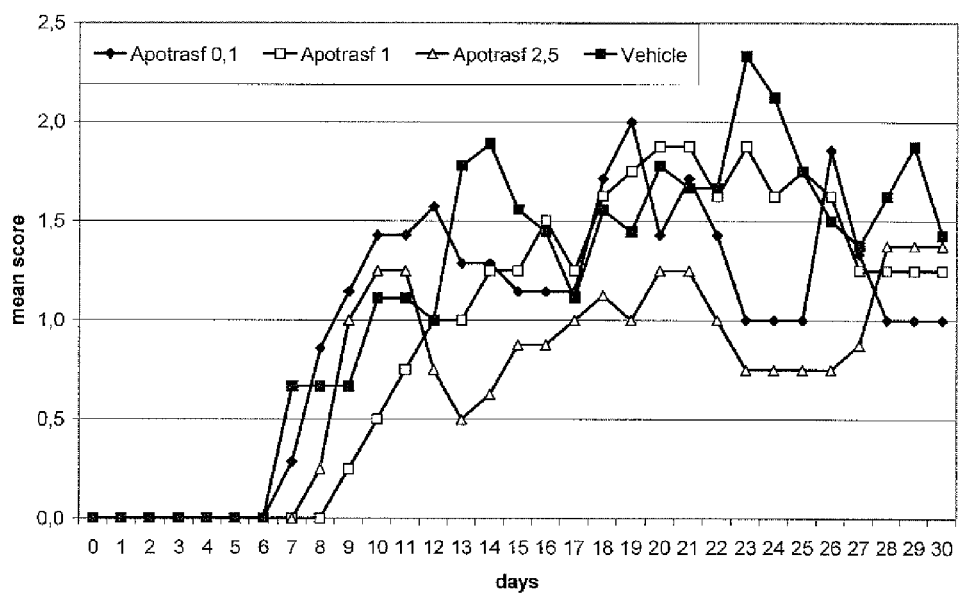

FIG. 7 A-B
A
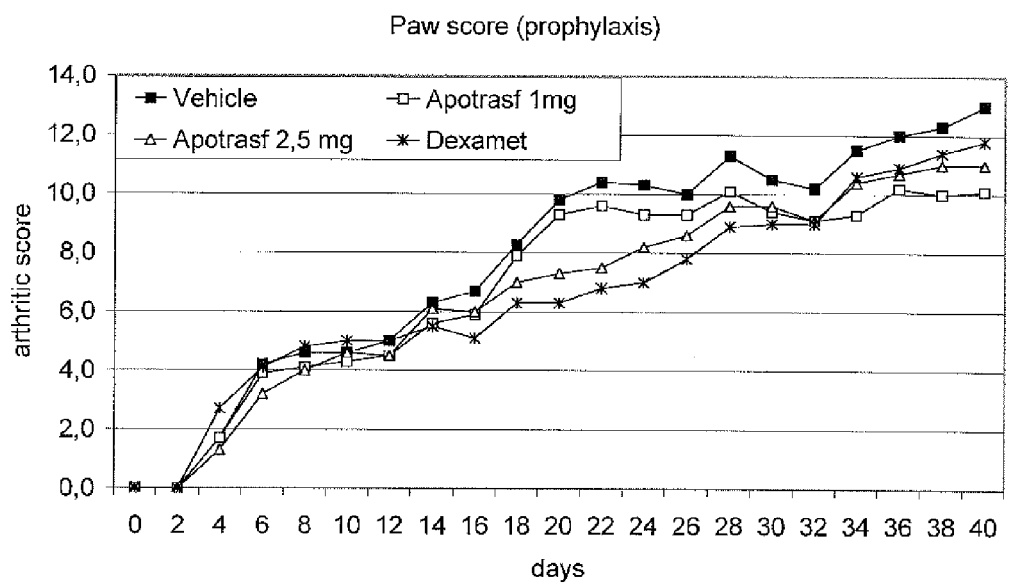
B
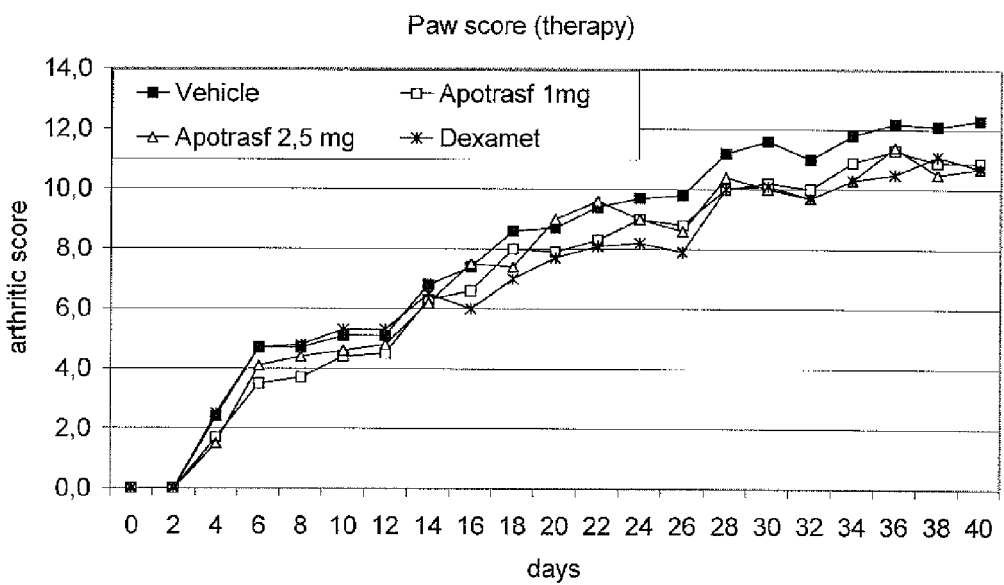

FIG. 7 C-D
C
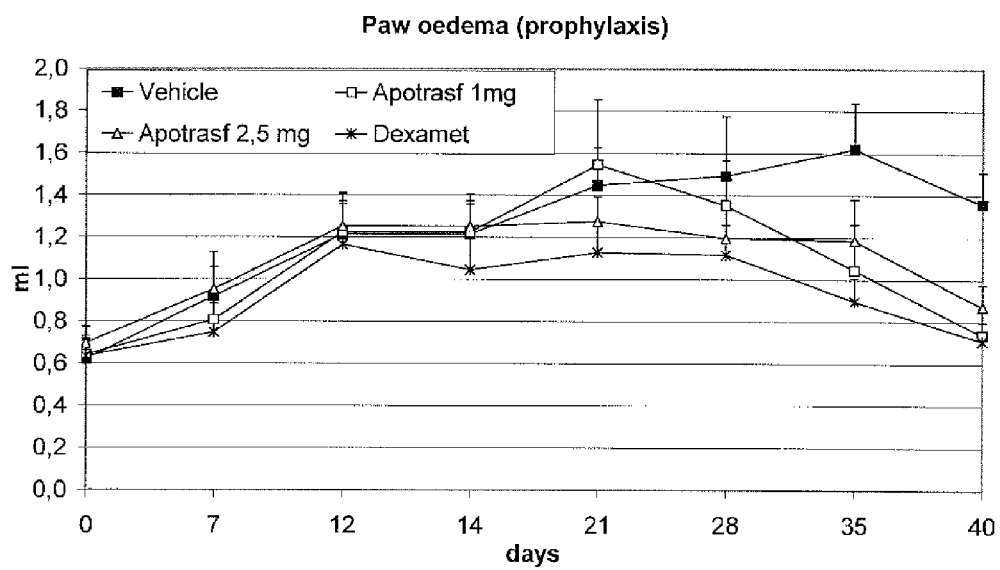
D
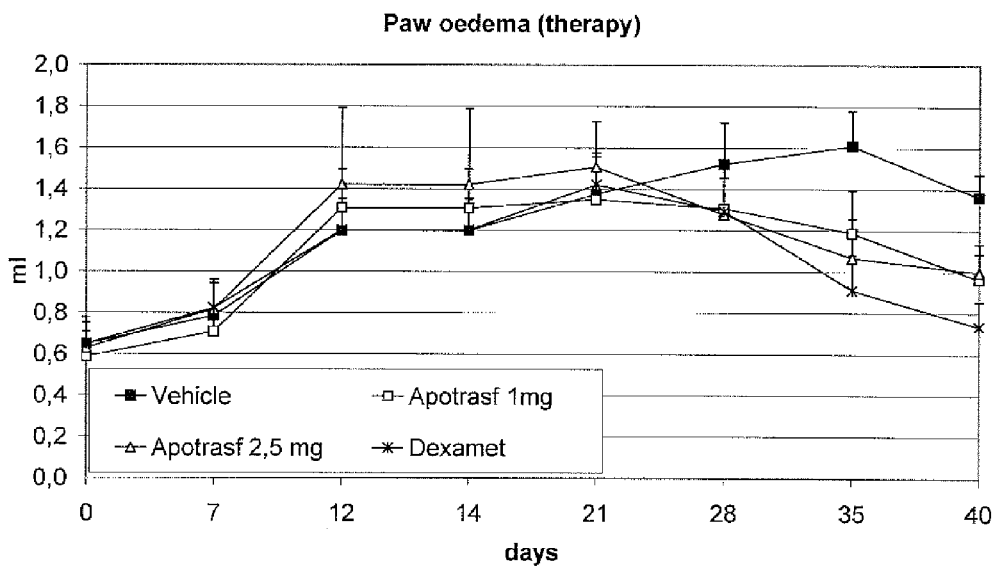

FIG 8 A-B
A
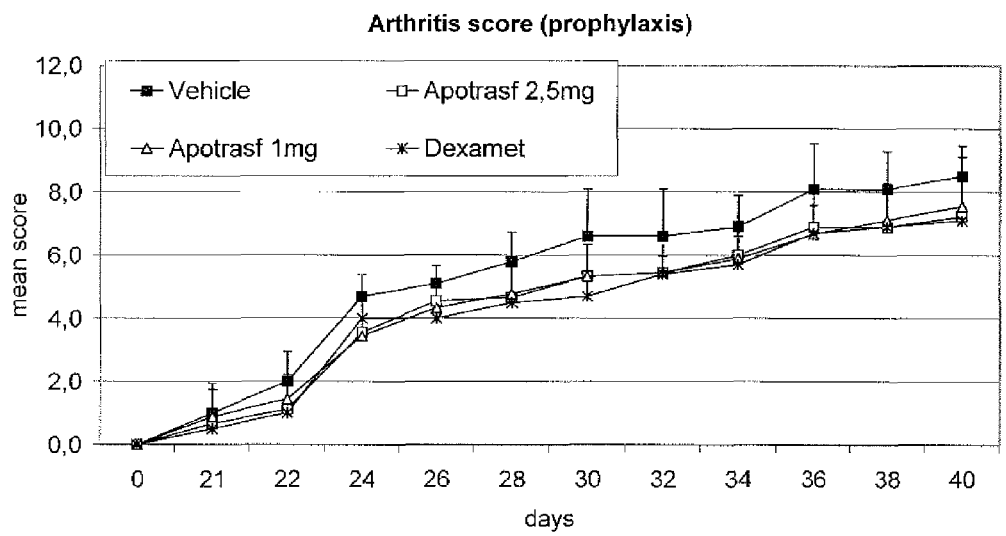
Arthritis score (prophylaxis)
B
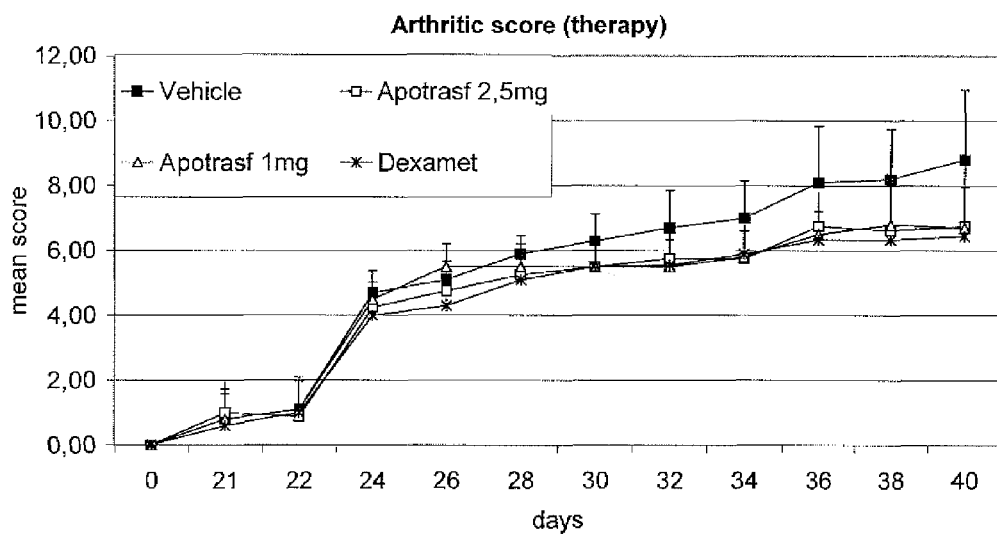
Arthritic score (therapy)

FIG 8 C-D
C
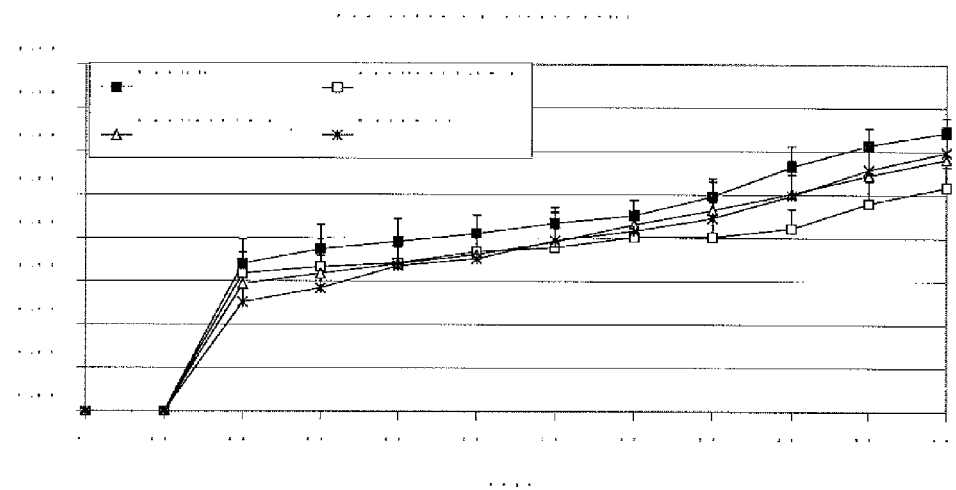
D
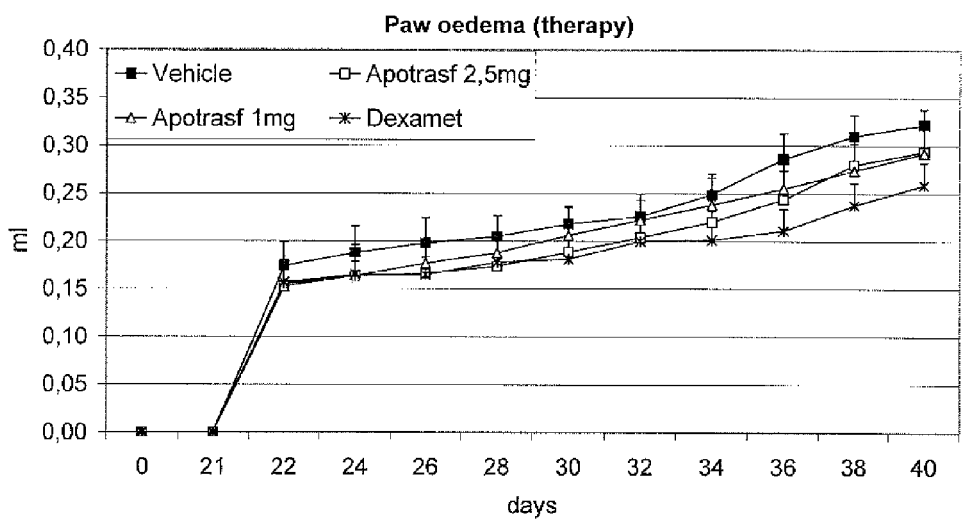

FIG 9 A
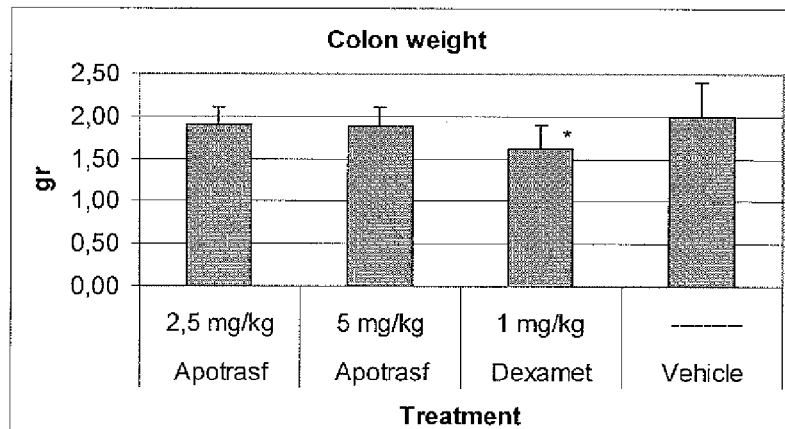
(a)
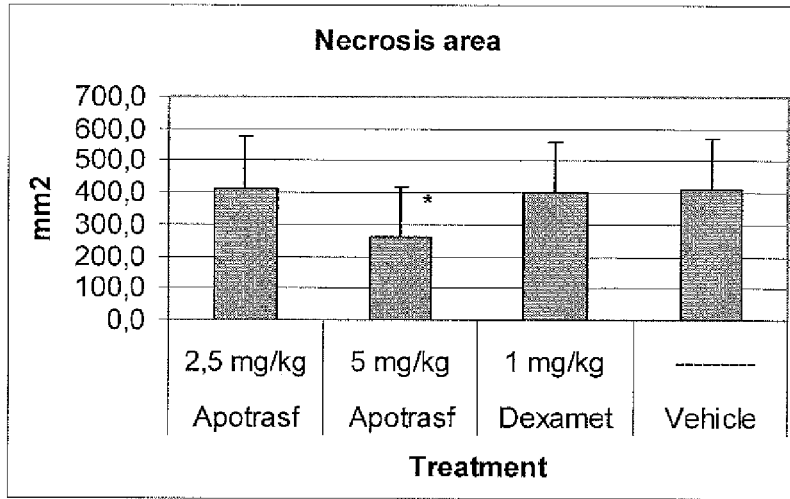
(b)
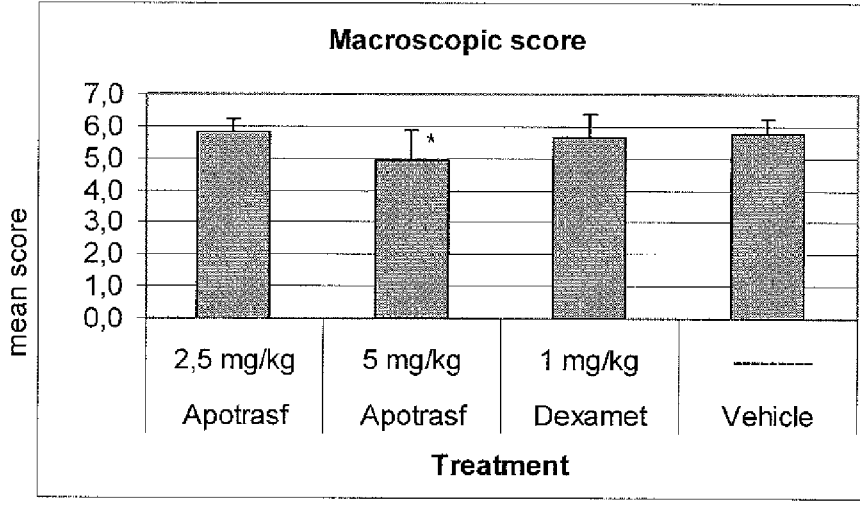
(c)

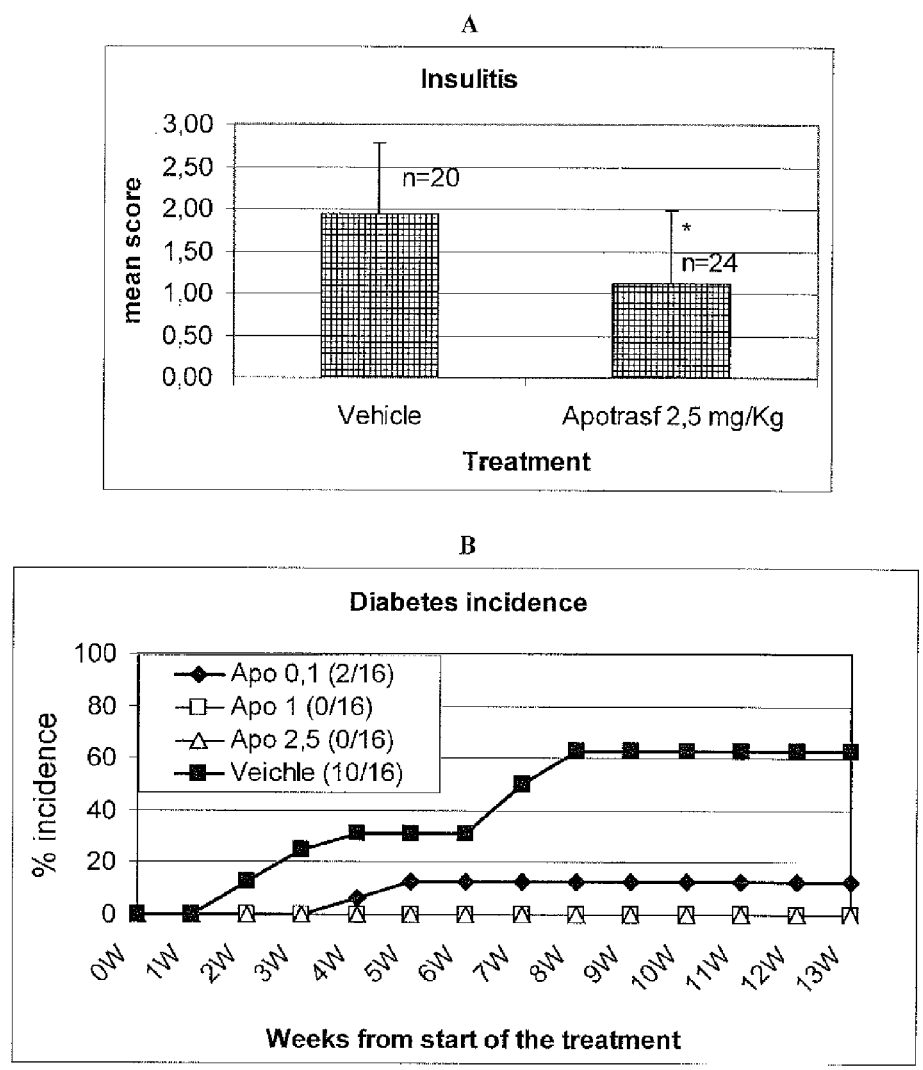
FIG. 10 A-B

FIG 10 C-D
C
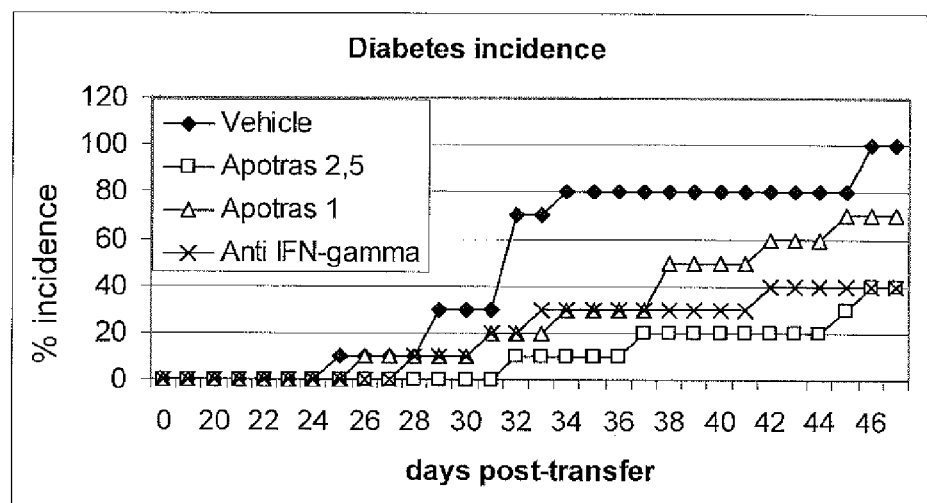
D
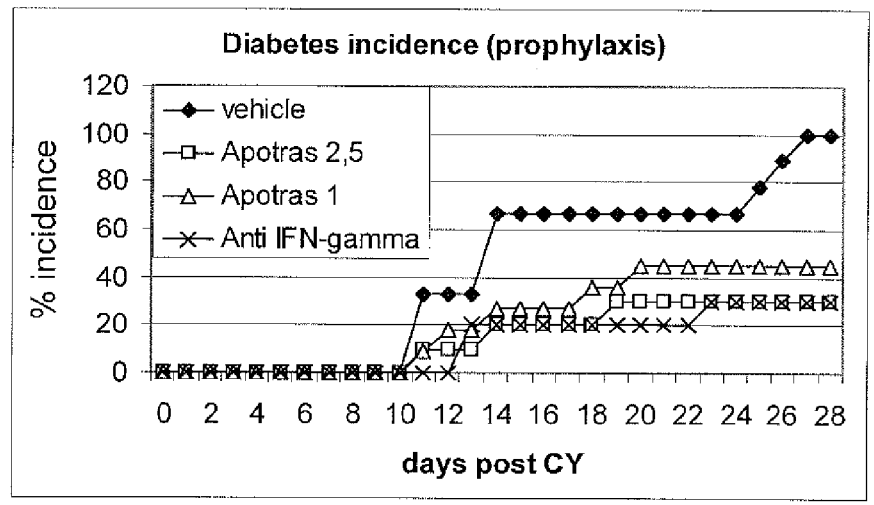

FIG 10 E-F
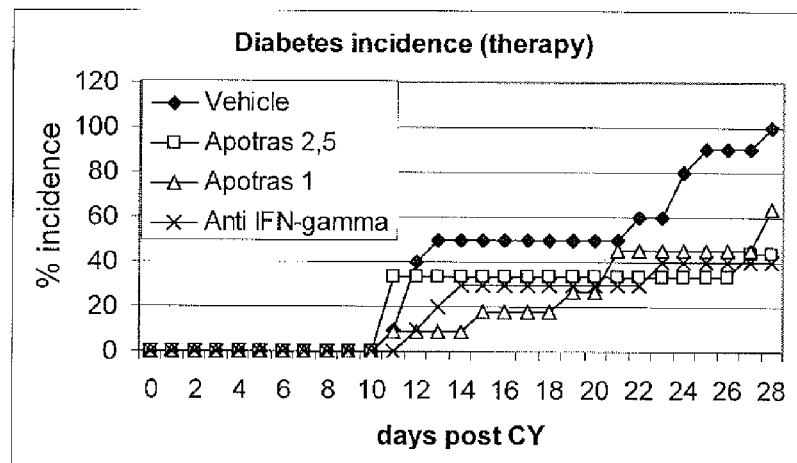
F
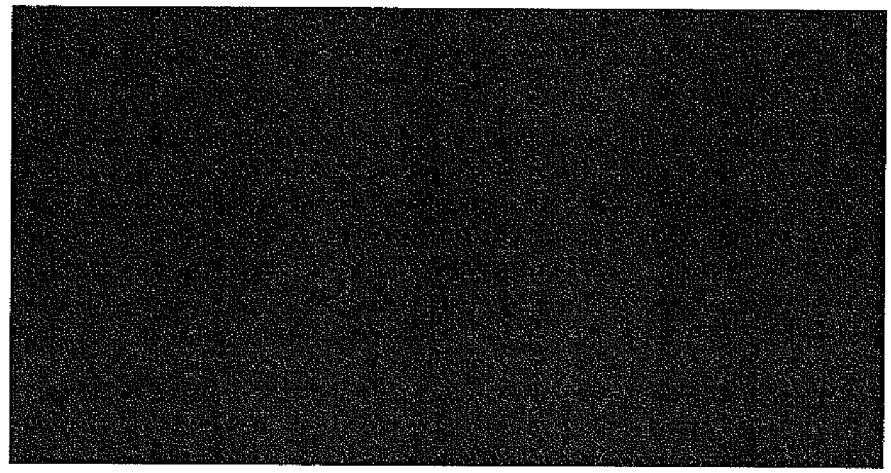

FIG 10 G-H
G
| | DIABETES ONSET | | | |
|---|---|---|---|---|
| | Apo 5 | Apo 2.5 | Apo 1.25 | PBS |
| Mean | 91,43 | 87,29 | 84,57 | 81,43 |
| St.Dev. | 9,6 | 16,8 | 13,8 | 10,1 |
| T-test | 0,082 | 0,444 | 0,635 | |
H
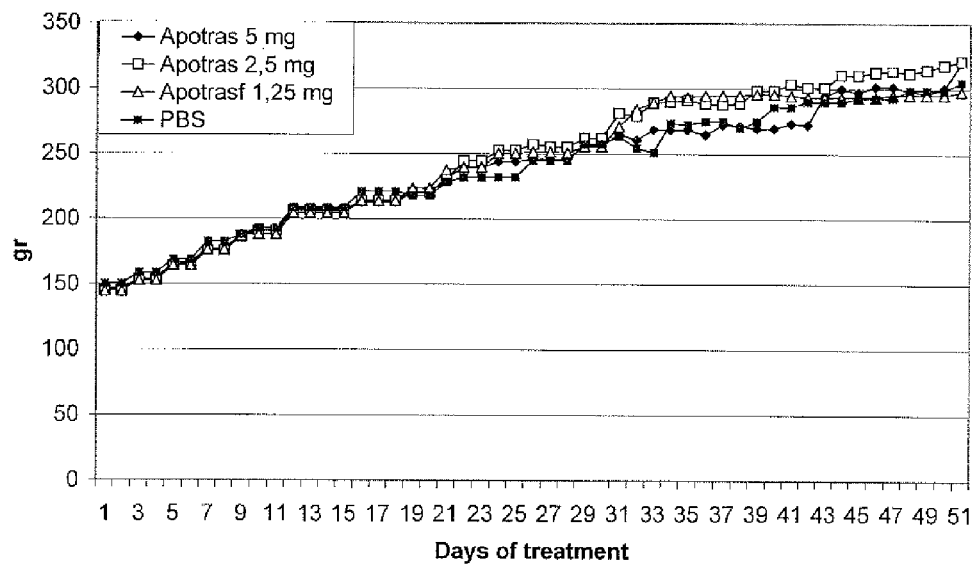
Body weight variation

TRANSFERRIN FOR USE IN THE TREATMENT AND/OR PROPHYLAXIS OF AUTOIMMUNE DISEASES

CROSS-REFERENCE TO RELATED APPLICATIONS

This application is a National Phase of PCT/IB2011/050623, filed Feb. 15, 2011, which claims priority from Italian Application FI2010A00020, filed Feb. 15, 2010, disclosures of which are incorporated herein by reference.

FIELD OF THE INVENTION

The present invention refers to the field of pharmaceutical compositions containing transferrin, useful in the treatment and/or prophylaxis of autoimmune diseases.

STATE OF THE ART

Autoimmune diseases form a group of diseases caused by an impairment of the immune system that makes it react against the body's own tissues.

The modification of the cell recognition mechanisms that normally enable the body to distinguish between the "self" and the "non-self", i.e. between elements that belong to the body and elements that are foreign to it, give rise to the production of antibodies, which can target single organs (organ-specific diseases) or trigger systemic disorders, damaging the individual's functions as a whole.

Briefly, the T-helper lymphocytes, which are an essential component of immune response, can be divided into two types, based on the combination of cytokines secreted in response to antigenic stimulation. The T-helper cell type I (Th1) clones secrete interleukin 2 (IL2), interferon-gamma (IFNγ) and lymphotoxin, while the T-helper cell type 2 clones (Th2) express interleukins 4, 5 and 6 (IL4, IL5, IL6). The differences in the pattern of cytokine secretion by Th1 and Th2 give rise to very different cell functions. Th1 and Th2 produce cytokines that are capable of mutually inhibiting one another: the IFNγ produced by Th1 inhibits the proliferation of the Th2 clones in vitro, while a cytokine called CSIF (cytokine synthesis inhibitory factor) can inhibit the proliferation of Th1 clones. These mutually inhibitory effects can be important in early immune response.

The prevalence of a Th2 response is typical of conditions of immune tolerance (e.g. physiological pregnancy and tolerance of transplants), while an increased Th1 response is characteristic of conditions of immunological intolerance.

In particular, Th1 cell activation is a feature of the development of various organ-specific autoimmune diseases (e.g. rheumatoid arthritis, multiple sclerosis, diabetes mellitus type I, thyroiditis, and Crohn's disease).

The capacity of the type 1 (Tc1) cytokines to stimulate immune response effector cells suggests that their overproduction, associated with a reduction in the type cytokines 2 (Tc2), may be one of the primary causes involved in the pathogenesis of autoimmune diseases. In particular, evidence from clinical experiments has demonstrated an increased output of type 1 cytokines in diabetes mellitus type 1, multiple sclerosis, Hashimoto's thyroiditis (Parish N M 1995), autoimmune liver diseases, and rheumatoid arthritis.

Given the above, it is easy to see that one of the goals of immunology is to succeed in regulating the Th1/Th2-Tc1/Tc2 balance in order to control the onset and progression of the above-mentioned diseases. This means that drugs capable of modulating cytokine production so as to inhibit type 1 cytokine response and stimulate type 2 response may have immunopharmacological qualities that would make them suitable for treating the above-mentioned diseases. In other words, blocking the Th1 cytokines and/or inducing a Th2 response could have a protective role in such cases.

This goal can currently be pursued by administering recombinant cytokines, cytokine antagonists or cortisone, but the administration of these molecules is often accompanied by toxic effects on various body systems.

Human transferrin is part of a large family of glycoproteins that are important components of the innate immune system, occurring in various secretory fluids, such as serum and breast milk.

Human transferrin (Tf) consists of a single polypeptide chain with 670-690 amino acid residues and a molecular weight of approximately 80 kDa. Transferrin binds two $Fe^{3+}$ ions with a high affinity ($K_d \approx 10\text{-}20$ M) together with two synergically associated anions. This means that four different isoforms of transferrin coexist in the plasma, which differ in iron content; using electrophoretic techniques, these forms can be separated and isolated into:

1) Apo-transferrin (APOTf, with no iron ions)
2) monoferric transferrin (with iron in the C-terminal domain)
3) monoferric transferrin (with iron in the N-terminal domain)
4) diferric transferrin (with iron in the two binding sites)

In physiological conditions, 30% of the transferrin in plasma is saturated with iron ions.

There are various known medical applications for pharmaceutical preparations containing human Tf for the treatment of various diseases.

Tf can dissolve the bond between insulin and its receptor in mammalian cells, so it has been used to treat hypoglycaemia, to inhibit insulin production and to reduce serum insulin levels in mammals (Vargas L. A. et al., U.S. Pat. No. 6,069,193).

Local applications of apo-transferrin (APOTf) have been used as a powerful inhibitor of bacterial adhesion on medical implants and to reduce implant-associated infections (Ardehali R. et al., U.S. Pat. No. 6,126,955).

Pharmaceutical preparations of Tf have been used as adjuvants with antibiotics to treat biofilm bacterial infections on prosthetic implants (Kedrion S. p. A., WO2008/142102).

APOTf has been used to reduce the high quantity of free iron in the serum of patients with malignant neoplastic diseases (e.g. leukaemia), or patients receiving cytotoxic treatments for cancer (high concentrations non-Tf-bound iron, NTBI, causes severe tissue damage in these patients) (Parkinen J. Et al., U.S. Pat. No. 6,326,473 B1).

Tf has also been used to combat the harmful effects of cytotoxic substances, anti-inflammatory substances, particularly aggressive antibiotics, and antineoplastic agents (Pierpaoli W., U.S. Pat. No. 6,328,966 B1).

Finally, the use of Tf, alone or in combination with erythropoietin, has been proposed for the treatment of anaemia, and particularly the anaemia associated with chronic infections, severe inflammatory conditions or cancer (Thomas L., US2003/0229012 A1).

In recent years, various studies have demonstrated that Tf also possesses immunomodulating properties.

Experiments performed on mixed lymphocyte cultures, induced to proliferate in response to stimulation with alloantigens, have demonstrated that Tf and Tf-derived glycans influence the proliferation of these cells (Lesnikova M, et al. J Hematother Stem Cell Res 2000, 9(3):381-92). Analysing the variations in the pattern of cytokines produced in response to stimulation with Tf has shown that this protein, and its glycan derivatives in particular, induce an upregulation of interleukin-10 (IL-10) and a downregulation of interleukin 1beta (IL-1β), TNF-α, IL-2 and IL-12. This has led to the deduction that Tf may be active in establishing a immune tolerance in allogeneic transplant recipients; in fact, pharmaceutical preparations containing pools of human transferrin have been used in combination with foreign tissue or cell transplants in mammals to induce a state of immune tolerance sufficient to minimise the risks of the so-called graft-versus-host disease (GvHD) (Pierpaoli W., U.S. Pat. No. 6,255,278 B1).

There is consequently an evident need to provide a valid alternative to the immunosuppressive treatments currently used in individuals with hyperactivated immune systems, i.e. in patients suffering from autoimmune diseases such as diabetes mellitus type 1, multiple sclerosis, rheumatoid arthritis, intestinal inflammatory diseases and autoimmune hepatitis. Another unsolved problem relating to these diseases concerns the shortage of effective drugs for their prevention, that can at least delay their onset.

DEFINITION AND ABBREVIATIONS

APOTf: apotransferrin
SMNCs: splenic mononuclear cells
ConA: Concanavalin A
TNF-α: tumour necrosis factor alpha
LPS: lipopolysaccharide
PBS: phosphate buffered saline
DNB: dinitrobenzene
PLP: proteolipid protein
Tf: transferrin

SUMMARY OF THE INVENTION

The present invention refers to the use of APOTf for the treatment and/or prevention of diseases characterised by immune system hyperactivation (a condition typical of autoimmune diseases). It has now been discovered and demonstrated that APOTf administration is effective in inducing a transition from the T-helper 1 immunological profile characteristic of patients with pictures of immune hyperactivation to the T helper 2 immunological profile typical of conditions of immune tolerance.

Subject-matter of the present invention are consequently pharmaceutical compositions containing APOTf for use in preventing (or delaying the onset) and treating autoimmune diseases. Based on the data obtained, the molecule has the surprising capacity to favourably modify the immune response profile both in vitro and in vivo. It is consequently feasible to use APOTf for the preparation of pharmaceutical compositions for use in treating, preventing and/or delaying the onset of autoimmune diseases such as diabetes mellitus type 1, multiple sclerosis, rheumatoid arthritis, intestinal inflammatory diseases and autoimmune hepatitis.

Being characterised by a good tolerability and availability, and relatively low costs, APOTf is consequently a valid alternative to the currently used immunosuppressive therapies.

According to the invention, daily administrations of APOTf in the range of 1 to 10 mg/kg body weight are preferable, in the range of 1 to 5 mg/kg body weight are even more preferable.

BRIEF DESCRIPTION OF THE FIGURES

FIG. 3: (a) Concentrations of TNF-α in SMNCs treated with APOTf; (b) Concentrations of IL-2 in SMNCs treated with APOTf;

FIG. 6: (a)-(b) Mean score as a function of time in experimental allergic encephalomyelitis (EAE) induced with PLP in SJL mice, treated with APOTf;

FIG. 7: (a) Effects of prophylaxis with APOTf on arthritis score progression in adjuvant-induced arthritis in the Lewis rat;

Figure 9:
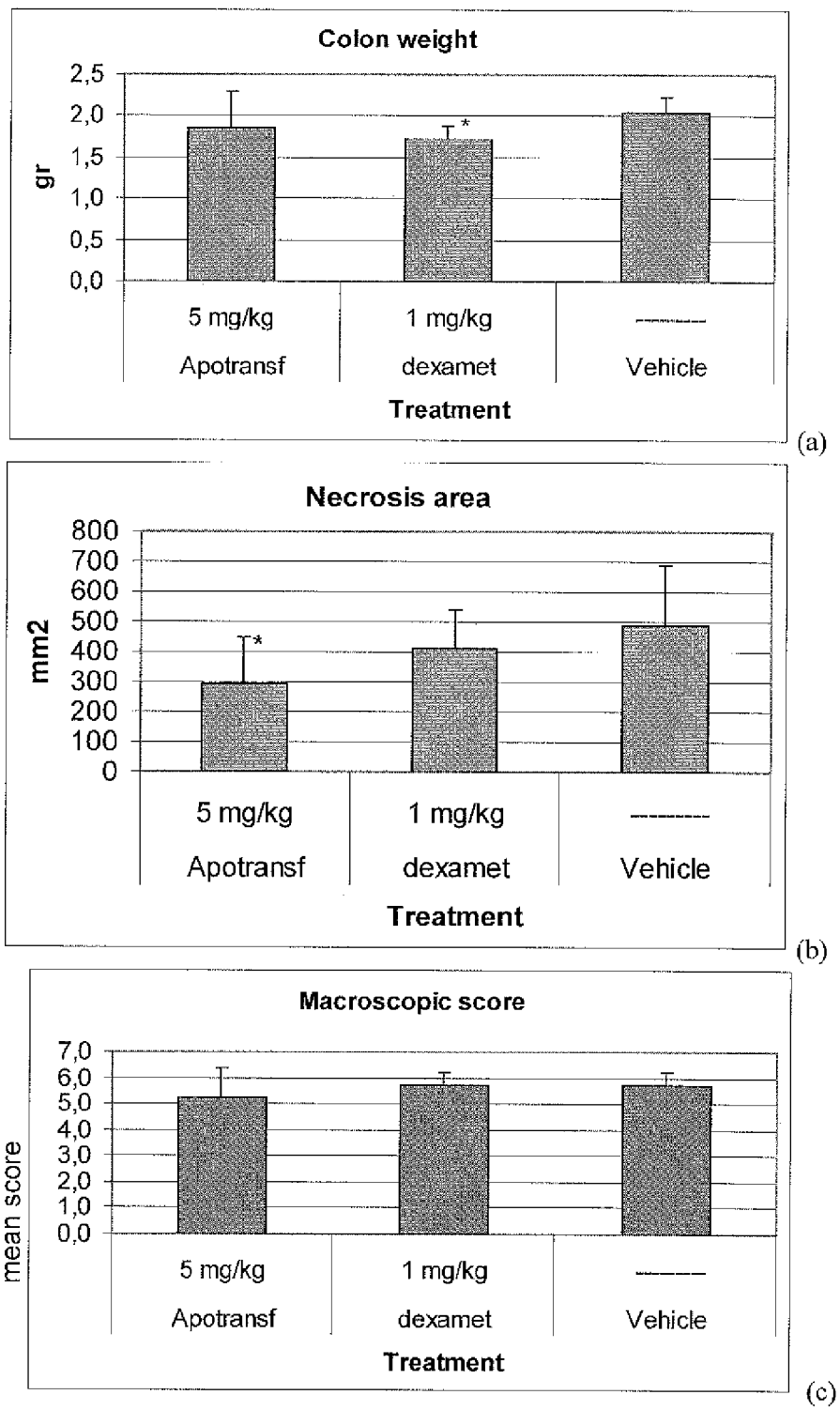
Figure 11:
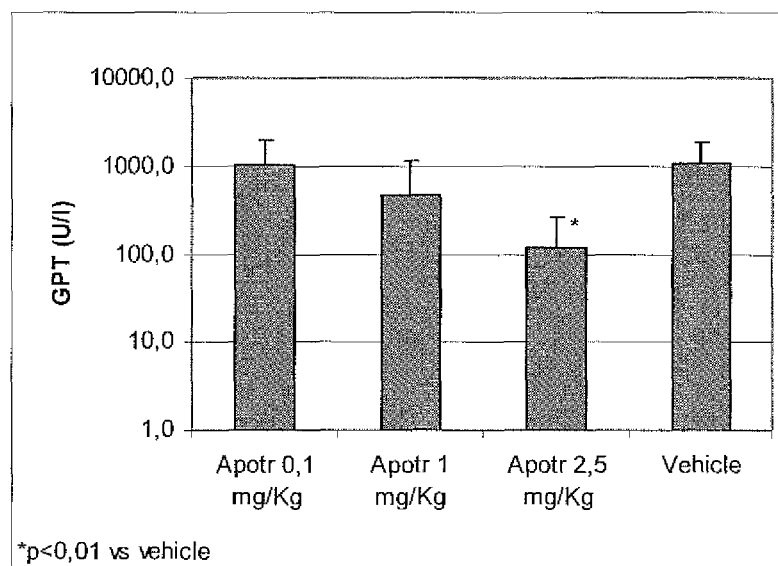

(b) Effects of APOTf administered for therapeutic purposes on arthritis score progression in adjuvant-induced arthritis in the Lewis rat;

(c) Effects of prophylaxis with APOTf on the development of oedema of the paw in adjuvant-induced arthritis in the Lewis rat;

(d) Effects of treatment with APOTf on the development of oedema of the paw in adjuvant-induced arthritis in the Lewis rat;

FIG. 8: (a) Effects of prophylaxis with APOTf on arthritis score progression in collagen-induced arthritis in DBA/1j mice;

(b) Effects of treatment with APOTf on arthritis score progression in collagen-induced arthritis in DBA/1j mice;

(c) Effects of prophylaxis with APOTf on the development of oedema of the paw in collagen-induced arthritis in DBA/1j mice;

(d) Effects of treatment with APOTf on the development of oedema of the paw in collagen-induced arthritis in DBA/1j mice;

FIG. 9: (a) Effects of APOTf on weight of colon, area of necrosis and macroscopic score in colitis induced by DNB;

(b) Effects of APOTf on weight of colon, area of necrosis and macroscopic score in colitis induced by DNB;

FIG. 10: (a): Mean histological score in pancreatic islets of 16-week-old NOD mice treated i.p. with APOTf at a dose of 2.5 mg/kg/day or with vehicle (sterile PBS) for 12 consecutive weeks six times a week;

(b) Percentage incidence of diabetes in 8- to 9-week-old NOD mice treated for 12 consecutive weeks with APOTf at doses of 0.1 mg/kg, 1 mg/kg, 2.5 mg/kg and with sterile PBS;

(c) Effects of APOTf on the development of diabetes induced by cell transfer in NOD mice;

(d) Effect of prophylactic treatment with APOTf on the development of diabetes induced by cyclophosphamide;

(e) Effects of early treatment with APOTf on the development of diabetes induced by cyclophosphamide;

(f) Incidence of diabetes in 36- to 45-day-old BB rats treated for 7 consecutive weeks with APOTf at doses of 1.25 mg/kg, 2.5 mg/kg, 5 mg/kg, and with PBS; the graph shows the cumulative survival as a function of days of life;

(g) Onset of diabetes in 36- to 45-day-old BB rats treated for 7 consecutive weeks with APOTf at doses of 1.25 mg/kg, 2.5 mg/kg, 5 mg/kg and with PBS;

(h) Variations in body weight of 36- to 45-day-old BB rats treated for 7 consecutive weeks with APOTf at doses of 1.25 mg/kg, 2.5 mg/kg, 5 mg/kg and with PBS;

FIG. 11: Mean serum values in experimental hepatitis induced with ConA in NMRI mice treated with APOTf.

DETAILED DESCRIPTION OF THE INVENTION

In particular, referring to the single autoimmune disease above said and to results of in vitro and in vivo experiments reported herein after, preferred daily administration of APOTf are:
multiple sclerosis: therapeutic regimen at ≥2.5 mg/kg body weight;
rheumatoid arthritis: prophylactic and therapeutic regimen at ≥1 mg/kg body weight;
intestinal inflammatory diseases: prophylactic and therapeutic regimen at ≥5 mg/kg body weight;
diabetes mellitus type 1: therapeutic regimen at ≥1 mg/kg body weight;
autoimmune hepatitis: prophylactic and therapeutic regimen at ≥2.5 mg/kg body weight.

The present invention is easier to understand in the light of the following examples of embodiments.

Example 1

In Vitro Assessment of Immunomodulatory Activity

We assessed the capacity of APOTf to modify certain functional parameters in vitro of lymphomonocytes of various type and origin, such as their proliferative response to mitogens and the production of pro-inflammatory cytokines and nitrites.

For the assessment of lymphomonocytic proliferation, a method was developed to separate the lymphomonocytes obtained from CBA and C57BL mouse spleens. The spleens were homogenized by passing them through a fine-mesh screen and subsequently submitted to centrifugation at 350 g for 5 minutes. The resulting cell pellet was resuspended in RPMI (Roswell Park Memorial Institute" medium) with 5% of FCS (Fetal Calf Serum), placed in a test tube, covered with Ficoll solution and centrifuged at 550 g for 18 minutes. The resulting ring of lymphomonocytes was collected from the Ficoll medium, washed twice to remove the residual Ficoll, resuspended in growth medium (a mixture of RPMI 1664, antibiotics and antimycotics, and 5% of FCS), and transferred to 96-well plates at a concentration of 500,000 cells/well. Each cell line, with or without mitogenic stimulation with ConA 2.5 µg/ml, was cultured without the drug or with one of three different concentrations of APOTf (6.25 µg, 12.5 µg, 25 µg per ml). The incubation period was protracted for 3 days, after which 1 µCi of tritiated thymidine was added to the cells. The residual radioactivity after 18 hours, established from a beta-counter reading, was considered as an indicator of proliferative response.

For the purposes of evaluating TNF-α and IL-2 secretion, splenic mononuclear cells from CBA, BALB/C and C57BL mice obtained as described previously were placed in standard growth medium at concentrations of $5 \times 10^6$ and $1 \times 10^7$ cells/well for a period of 48 hours, with or without mitogenic stimulation (ConA 2.5 µg/ml) and with or without transferrin (12.5 µg/ml). The TNF-α and IL-2 were measured using the ELISA test. The sensitivity limit for these tests was 15 pg/ml.

The results obtained are shown in FIGS. 3A and 3B.

To assess the effects of the drug in question on the production of nitrites, splenic mononuclear cells from BALB/c mice, obtained as described previously, were placed in standard medium at concentrations of 5×106 and 1×107 cells/well, with or without mitogenic stimulation (ConA 2.5 µg/ml), and without the drug or with one of three different concentrations of APOTf (6.25, 12.5, 25 µg/ml) for an incubation period of 48 hours.

The concentrations of NO in the splenic mononuclear cell cultures were identified by colorimetric assay exploiting the Griess reaction, which is able to determine the quotient of nitrites in the cell surnatant, with or without mitogenic stimulation (ConA 2.5 mg/ml). For this purpose, in particular, 50 ml of Griess reagent were added to 50 ml of surnatant and, after 10 minutes, the consequent colorimetric reaction was measured with an ELISA reader at 570 nm.

The sensitivity limit for this assay was around 0.5 mM/ml.

Figure 1:
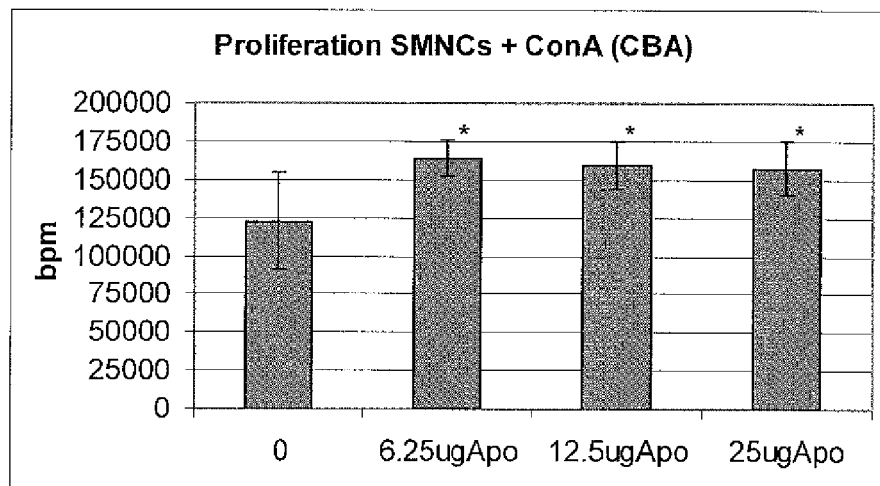
FIG. 1: Proliferation of SMNCs from C57Bl mice stimulated with ConA and treated with APOTf.
Figure 2:
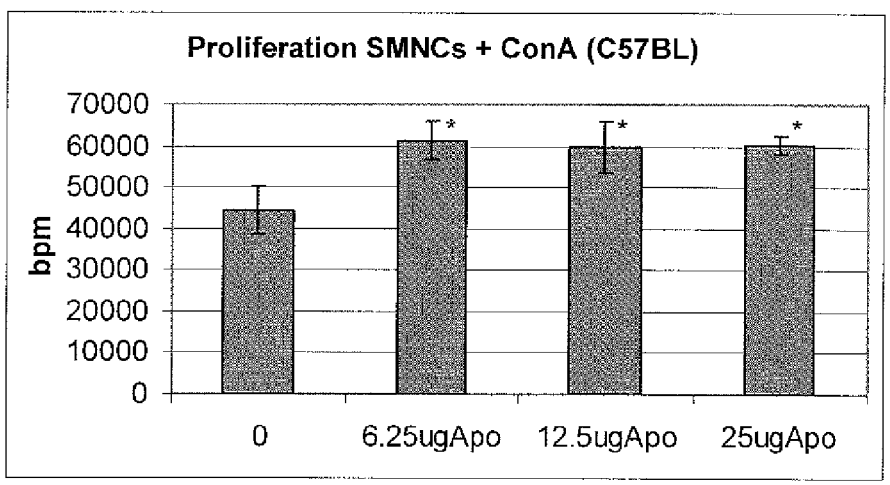
FIG. 2: Proliferation of SMNCs from CBA mice stimulated with ConA, and treated with APOTf.
Figures 4, 5:
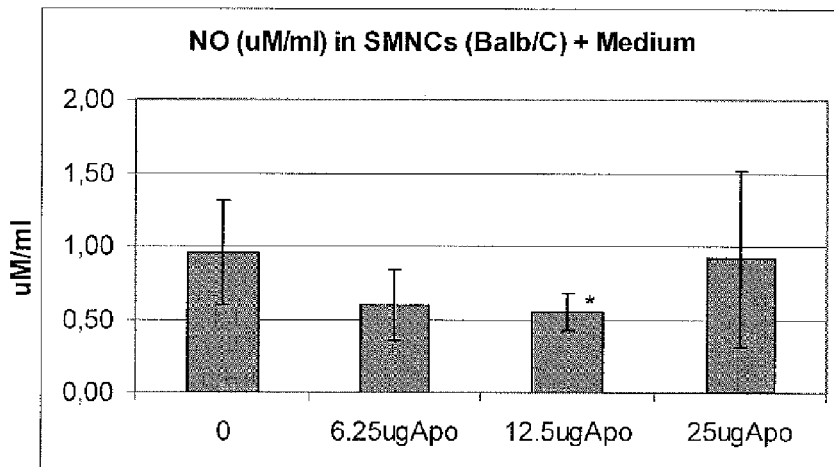
FIG. 4: Concentrations of NO (μM/ml) in SMNCs treated with APOTf.
FIG. 5: (a) Mean concentrations of IL-1β in PCs treated with APOTf; (b) Mean concentrations of TNF-α in PCs treated with APOTf.

The results obtained are shown in FIG. 4

The immunomodulatory capacity of the molecule was also tested on peritoneal lymphomonocytes from CBA, BALB/C and C57BL mice. Briefly, peritoneal cells were isolated from the abdominal cavity of CBA, BALB/c, C57BL mice by means of an intraperitoneal injection of 1 ml of PBS, followed by the collection by aspiration of the whole quantity of PBS, including the peritoneal cells, which was placed in a test tube and centrifuged at 350 g for 5 min. Then the cells were counted and placed in complete growth medium (RPMI 1640 [Gibco], with 200 mM of 1% L-glutamine, 10000 U/m of 1% penicillin-streptomycin and 5% FCS) in 24-well plates.

Two different sets of cell cultures were prepared to determine the levels of TNF-α:
CBA mouse peritoneal cells were placed in a culture at a mean concentration of 1×106 cells/well and simultaneously stimulated with LPS (5 µg/ml) for 48 hours with or without APOTf (12.5 µg/ml);
peritoneal cells from BALB/c mice and C57BL mice were placed in a culture at a mean concentration of $5 \times 10^6$ cells/well, and incubated for 24 hours with or without LPS (5 µg/ml), and with or without APOTf (12.5 µg/ml).

The concentration of TNF-α was established using the ELISA test with a sensitivity limit of 15 pg/ml.

For the purpose of assessing the production of interleukin-1β (IL-1β), CBA mouse peritoneal cells were divided into two sets, placed in culture at a mean concentration of 1,000,000 cells/well and simultaneously stimulated with LPS (5 µg/ml) for a period of 5 or 24 hours, with or without APOTf (12.5 µg/ml).

The concentrations of IL-1β were ascertained using ELISA.

The results obtained are shown in FIG. 5.

The analysis of the effects of APOTf on the functional parameters of the lymphomonocytes in question demonstrated that the molecule has an pleiotropic biological immunomodulatory activity on all the cell types when used in the range of concentrations examined.

In fact, APOTf is effective in modifying proliferative response, cytokine secretion and nitrite production by lymphomonocytes of various origin in vitro.

In particular, the data in our possession suggest that an increase in the absolute number of lymphomonocytes coincided not with a parallel increase in their functional activity, but with a reduction instead, as demonstrated by the low levels of TNF-α and IL-2 detected in the cultures considered.

Example 2

Assessment of Efficacy in an Animal Model of Multiple Sclerosis

We assessed the effects of administering APOTf in vivo in a murine model of EAE (Experimental Autoimmune Encephalomyelitis) in SJL mice, considered the model most closely resembling human multiple sclerosis, of which it faithfully reproduces many immunobiological, clinical and histopathological aspects.

Briefly, the disease was induced in female SJL mice 6 to 7 weeks old, which—after undergoing a one-week period of adaptation to the stabling conditions, involving standard laboratory conditions with free access to food and water, and controlled conditions of temperature and humidity—were inoculated subcutaneously (s.c.), under anaesthesia, at two different axillary lymph node draining sites with 75 μg/mouse of PLP (Genemed Synthesis San Francisco, Calif.) dissolved in saline solution and emulsified in a ratio of 1:1 with Freund complete adjuvant (FCA) containing 0.6 mg of *Mycobacterium tuberculosis* strain H37RA. On day 0 and day 2 after immunisation, the animals were also inoculated intraperitoneally (i.p.) with 200 ng/mouse of pertussis toxin. They were then divided by means of a randomisation process into groups and treated with i.p. APOTf at doses of 0.1, 1 and 2.5 mg/kg, and with the corresponding vehicle (sterile PBS) once a day starting from the 7th day after induction and up until the 30th day. The animals were checked daily by an observer unaware of the treatment, who recorded their weight and assessed their clinical disease parameters according to the following criteria: 0=no clinically evident symptoms; 1=flaccid tail and/or mild rear limb weakness; 2=flaccid tail with moderate rear limb weakness; 3=severe rear limb weakness and mild front limb weakness; 4=rear limb paralysis with moderate front limb weakness; 5=tetraplegia and/or animal dying. The significant parameters for the purposes of assessing the effects of the drug were: mean cumulative score; mortality index; time of onset of disease; duration of disease. FIG. 6 shows the course of the disease recorded in two different experiments conducted using the same experimental procedures. The analysis of the effects of APOTf on the clinical disease parameters in question, particularly when administered at a daily dose of 2.5 mg/kg starting from the 7th day after induction of the disease, and thus according to a therapeutic regimen, showed that the molecule has the capacity to favourably influence the course of the experimental allergic encephalomyelitis, reducing both the mean cumulative score and the duration of the disease in the animals in question. The treatment was also well tolerated, since there was no significant difference in the mortality rates between the groups.

Pharmaceutical preparations containing APOTf could therefore be used for the treatment of multiple sclerosis.

Example 3

Assessment of Efficacy on Animal Models of Rheumatoid Arthritis

We evaluated the effects of administering APOTf in vivo on animal models of rheumatoid arthritis, such as the arthritis induced by adjuvant in Lewis rats and the arthritis induced by collagen type 2 in C57BL/6 mice.

Concerning the former, microscopic joint alterations tend to become clinically evident within 14 days of induction. The severity of the disease usually increases in the first two weeks, then diminishes gradually over the course of 1-3 weeks afterwards. Joint swelling and deformity may also persist in the longer term, particularly involving the ankle. This model of disease shares significant features with human rheumatoid arthritis: in fact, AIA (Adiuvant-Induced Arthritis) is an inflammatory disease immunologically mediated by T cells and macrophages.

Briefly, the disease was induced in male Lewis rats aged between 8 and 12 weeks and weighing between 170 g and 215 g, which—after undergoing a one-week period of adaptation to the stabling conditions, involving standard laboratory conditions with free access to food and water, and controlled conditions of temperature and humidity—were inoculated intradermally (i.d.) at the base of the tail with an emulsion comprising a total volume of 100 μl, containing 0.3 mg of heat-killed *Mycobacterium tuberculosis* strain H37Ra and Freund incomplete adjuvant.

The animals were then divided by means of a randomisation process into groups and treated according to a prophylaxis regimen six times a week, starting from the day after induction of the disease and up until 30 days after induction, with i.p. APOTf at doses of 1 and 2.5 mg/kg, with the corresponding vehicle (sterile PBS) and with dexamethasone at a dose of 0.3 mg/kg, or according to a therapeutic regimen adopting the same experimental design but starting from the 10th day after induction and up until the 30th day. The animals were checked on alternate days by an observer unaware of the treatment, who recorded their weight and assessed their clinical disease parameters according to the following criteria:

0=no clinically evident signs of arthritis;
1=swelling and/or redness of a paw or digit;
2=involvement of two joints;
3=involvement of more than two joints;
4=severe arthritis of whole paw and digits.

The clinical arthritis index for each animal was calculated by combining the four scores for each paw.

Clinical severity was also established by quantifying the weekly variation in paw volume by plethysmometry (model 7140; Ugo Basile). The results are shown in FIGS. 7A, 7B, 7C and 7D.

The activity of APOTf was subsequently evaluated on arthritis induced by collagen type 2. An advantage of this model of arthritis over other models of arthritis, such as the one induced by adjuvant, lies in the development of an arthritis-generating response to a clearly-defined antigen (collagen type II), which also enables the study of antigen-induced immunological phenomena and their selective modifications induced by pharmacological treatments.

Briefly, the disease was induced in male DBAJ/1 mice between 8 and 9 weeks old, which—after undergoing a one-week period of adaptation to the stabling conditions, involving standard laboratory conditions with free access to food and water, and controlled conditions of temperature and humidity—were inoculated intradermally (i.d.) at the base of the tail with an emulsion comprising a volume of 100 μl containing 100 μg of bovine collagen type II emulsified in Freund complete adjuvant. On day 20 after immunisation, the animals received a second i.d. inoculation of 100 μg of collagen type II dissolved in PBS for a total volume of 100 μl.

They were then divided into groups using a randomisation process and treated i.p. according to a prophylactic regimen six times a week, starting from the day after induction of the disease and up until post-induction day 30, with APOTf at doses of 1 and 2.5 mg/kg, with the corresponding vehicle (sterile PBS), and with dexamethasone at a dose of 0.3 mg/kg, or according to a therapeutic regimen adopting the same experimental design but starting from the 22nd day after induction and continuing up until the 30th.

The same disease assessment criteria were applied as described previously for adjuvant-induced arthritis.

The results are shown in FIGS. 8A, 8B, 8C and 8D.

The analysis of the effects of APOTf on the parameters examined showed that it is effective in reducing both the clinical score for the disease and the mean volume of the paw in both the animal models of rheumatoid arthritis and with both the drug administration regimens considered, especially at a dose of 2.5 mg/kg. In fact, the results were similar to those obtained with the medication used as a positive control, i.e.

dexamethasone. The treatment was also well tolerated, as shown by the absence of any significant differences in the animals' bodyweight or the number of lethal events recorded by comparison with the group treated with the vehicle.

Thus, pharmaceutical preparations containing APOTf could be used for the treatment of human rheumatoid arthritis and in general of diseases involving joint damage with an immunoinflammatory pathogenesis.

Example 4

Assessment of Efficacy in an Animal Model of Intestinal Inflammatory Disease

We assessed the effects of administering APOTf in vivo on colitis induced by dinitrobenzene sulphonic acid (DNBS) in Lewis rats. In this model, a single intracolonic administration of DNBS triggers the onset, within 4 days, of a pathological condition with clinical and immunohistological characteristics entirely similar to those seen in human intestinal inflammatory diseases, such as Crohn's disease and ulcerous rectocolitis. These include extensive damage to the colon, with areas of hyperaemia, oedema and ulceration, as well as an increase in the weight of the colon, which is microscopically characterised by the presence of necrosis, inflammation and fibrosis. As in its human counterpart, it seems that activation of the T cells and macrophages, accompanied by an overproduction of pro-inflammatory cytokines type 1, such as TNF-α, is the main pathogenic mechanism behind the condition.

Briefly, the disease was induced in male Wistar rats weighing between 200 and 250 g, which—after undergoing a one-week period of adaptation to the stabling conditions, involving standard laboratory conditions with free access to food and water, and controlled conditions of temperature and humidity—on day 0, after 24 hours of fasting and under mild anaesthesia, were administered intracolonically (i.c.) a solution containing 0.25 mL of 50% ethanol with 30 mg of DNBS by means of a catheter with an external diameter of 0.3 mm positioned approximately 7 cm proximally to the anus. After the DNBS administration, 0.5 ml of air were insufflated and the catheter was removed. The animals were then kept for approximately 30 seconds in a Trendelenburg position.

The animals were divided into groups using a randomisation process and treated i.p. with APOTf at daily doses of 2.5 and 5 mg/kg, with the corresponding vehicle (sterile PBS) and with dexamethasone at a dose of 1 mg/kg, for five consecutive days, starting from the day before induction (days −1, 0, 1, 2 and 3). The animals were sacrificed on the fourth day after induction (day 4) by $CO_2$ inhalation and the segment of colon corresponding to the distally terminal 10 cm was harvested. The colon was emptied of any enteral material contained in the cavity then weighed, cut longitudinally and opened for weighing, to assess the area of damaged mucosa (ADM), corresponding to the area of macroscopically visible necrosis, with the aid of a calibre, and to assess the microscopic damage score (MDS) according to the following criteria: 0=no damage; 1=localised hyperaemia and/or oedema; 2=linear ulcer <half the circumference of the colon; 3=linear ulcer >half the circumference of the colon; 4=circular ulcer <1 cm; 5=circular ulcer between 1 and 2 cm long; 6=circular ulcer >2 cm long.

The animals' body weight was also recorded, both on the day of induction and on the day of death.

The results of two exemplary experiments, performed using the same experimental design, are shown in FIGS. 9A and 9B.

The analysis of the effects of APOTf on the parameters considered showed that, when administered at 5 mg/kg, it is effective in reducing both the area of necrosis and the microscopic damage score associated with the disease. In fact, the results were comparable, and in some cases even better than those obtained with the medication used as a positive control, i.e. dexamethasone, which only proved able to reduce the weight of the colon.

For these reasons, pharmaceutical preparations containing APOTf could be used for the treatment of human inflammatory intestinal diseases.

Example 5

Assessment of Efficacy in Animal Models of Diabetes Mellitus Type I

We assessed the capacity of APOTf to influence the onset and course of diabetes mellitus type 1 in various animal models, in spontaneous form, accelerated with the transfer of splenic cells from syngenic diseased animals, or induced by administering cyclophosphamide in NOD mice, and spontaneous diabetes in BB rats.

NOD mice spontaneously develop a diabetes mellitus mediated by T-cell dependent autoimmune mechanisms at between 80 and 200 days of life, with an incidence of 80% in females and 10-20% in males. The clinically manifest onset of diabetes is preceded by an inflammatory infiltration of the pancreatic islets (insulitis), which can generally be identified on histological examination starting from 4-6 weeks of life. In some mouse strains it is also possible to induce an accelerated form of cell-mediated autoimmune diabetes by transferring splenic cells from diabetic NOD mice to syngenic euglycaemic animals, or by means of one or more injections (200-300 mg/kg) of cyclophosphamide administered with a two-week interval between them.

To assess the effects of APOTf on spontaneous diabetes in NOD mice, 4 or 8-9 week-old female mice of said strain underwent a one-week period of adaptation to the stabling conditions, involving standard laboratory conditions with free access to food and water, and controlled conditions of temperature and humidity before the experiment; then they were respectively treated intraperitoneally with APOTf at a dose of 2.5 mg/kg, and with the corresponding vehicle (sterile PBS) for six days a week for 12 consecutive weeks, or with APOTf at doses of 0.1 mg/kg, 1 mg/kg, 2.5 mg/kg, and the corresponding vehicle (sterile PBS), according to the same experimental design.

During the study period, the mice were checked twice a week for the onset of diabetes by measuring their glycosuria: then they were confirmed as being diabetic when their fasting glycaemia levels were found higher than 12 mmol/l on two consecutive days.

The animals that began the treatment at 4 weeks old were sacrificed by $CO_2$ inhalation at the end of the treatment period and their pancreas was harvested for histological assessment.

This histological examination of the pancreatic islets was conducted with reference to a sample scale according to the following criteria:
0=no mononuclear cell infiltrate;
1=periductal mononuclear cell infiltrate;
2=peri-insular mononuclear cell infiltrate;
3=intra-insular mononuclear cell infiltrate;
4=intra-insular mononuclear cell infiltrate associated with beta-cell distribution.

At least 12 islets were examined for each mouse, while the mean histological score for each pancreas was obtained by dividing the total score by the number of islets examined.

The results obtained from the means of two separate experiments are presented in FIGS. 10A and 10B.

To assess the effects of APOTf on accelerated diabetes in NOD mice, 5 or 13-14 week-old female mice of this strain underwent a one-week period of adaptation to the stabling conditions, involving standard laboratory conditions with free access to food and water, and controlled conditions of temperature and humidity before the experiment; then diabetes was induced either by means of the intravenous transfer (to the tail vein) of splenic cells isolated from diabetic NOD mice into euglycaemic NOD mice, at a concentration of $2.5 \times 10^6$ cells/mouse, or by means of two intraperitoneal injections of cyclophosphamide at a dose of 200 mg/kg, administered 14 days apart.

The onset of diabetes was identified by means of daily glycosuria measurements, diagnosing animals as diabetic when, after two positive glycosuria tests, their fasting glycaemia was found higher than 12 mmol/l on two consecutive days. The animals were assessed for glycosuria on alternate days throughout the course of the experiment.

For the model of accelerated diabetes induced by cell transfer, the animals were randomised to be treated intraperitoneally (i.p.) with rat monoclonal antibody or mouse anti-IFN-gamma (AN-18) at a dose of 500 µg/mouse on alternate days (as a positive control), with APOTf at doses of 1 mg/kg and 2.5 mg/kg, or with the corresponding vehicle (sterile PBS), starting from the seventh day after the cell transfer, six times a week for six consecutive weeks.

For the accelerated diabetes induced by cyclophosphamide inoculation, the animals were randomised and treated intraperitoneally (i.p.) with APOTf at doses of 1 and 2.5 mg/kg, with the corresponding vehicle (sterile PBS) six times a week for 28 days, and with anti-IFN-γ monoclonal antibody AN-18 at a dose of 500 µg/mouse on alternate days for 28 consecutive days, according to a prophylactic regimen, or using the same molecules and the same experimental design but starting from the seventh day after cyclophosphamide inoculation and throughout the experimental period up until the 28th day. In both cases the animals were euglycaemic at the start of the therapy.

The results obtained from the means of two separate experiments are presented in FIGS. 10C, 10D and 10E.

Like NOD mice, BB rats spontaneously develop insulin-dependent diabetes mellitus due to the destruction of the pancreatic islet mediated by autoreactive T cells. Here again, clinically manifest disease is preceded by an inflammatory infiltration of the pancreatic islets, but diabetes develops acutely at between 60 and 120 days of life, with an incidence of 60-80% in both males and females.

To assess the effects of APOTf on spontaneous diabetes in the BB rat, male rats of this strain aged between 37 and 46 days of life first underwent a one-week period of adaptation to the stabling conditions, involving standard laboratory conditions with free access to food and water, and controlled conditions of temperature and humidity before the experiment; then they were treated with i.p. APOTf at doses of 1.25 mg/kg, 2.5 mg/kg, 5 mg/kg, and with the corresponding vehicle (sterile PBS) every day for seven consecutive weeks.

The onset of diabetes was assessed by measuring glycosuria and diagnosing as diabetic any animals with a fasting glycaemia found higher than 12 mmol/l on at least two consecutive days.

The results obtained from the means of two separate experiments are presented in FIGS. 10F, 10G and 10H.

The analysis of the effects of APOTf on the parameters examined showed that, especially when administered at a dose of 2.5 mg/kg, it is effective in reducing both the insulitis and the incidence of diabetes according to the experimental design adopted in the models of diabetes mellitus type 1, be it spontaneous or accelerated by cell transfer or cyclophosphamide inoculation, in NOD mice.

In the light of the above, pharmaceutical preparations containing APOTf could be used for the prevention and treatment of diabetes mellitus type 1 in humans.

Example 6

Assessment of Efficacy in Animal Models of Autoimmune Hepatitis

We evaluated the effects of administering APOTf in vivo on hepatitis induced by ConA in NMRI mice, which represent a useful model of numerous human liver diseases with an immunoinflammatory pathogenesis.

In this model, a single injection of ConA suffices to develop immunomediated liver lesions. In fact, within 8-24 hours of ConA administration, the pathological picture is characterised by clinical and histological signs of hepatitis with an increased transaminase activity in the plasma, intralobular inflammatory infiltration with a massive accumulation of granulocytes, and necrotic changes in the liver cells. The hepatitis induced by ConA is dependent both on the CD4+ T cells and on the macrophages.

Briefly, the disease was induced in male NMRI mice aged between 6 and 7 weeks, which—after undergoing a one-week period of adaptation to the stabling conditions, involving standard laboratory conditions with free access to food and water, and controlled conditions of temperature and humidity—on day 0, after a 16-hour fast, after inducing mild anaesthesia, were inoculated intravenously (i.v.) through the tail vein with 20 mg/kg of ConA dissolved in sterile PBS.

They were divided into groups by means of a randomisation process and treated with i.p. APOTf at doses of 0.1, 1 and 2.5 mg/kg, and with the corresponding vehicle (sterile PBS) 24 hours and then 1 hour before inoculation with ConA, and they were sacrificed 8 hours after inoculation with ConA to collect peripheral venous blood samples. Glutamate-pyruvate transaminase (GPT) activity in the plasma was then determined using a photometric standard, tested using the chromatic analyser.

The results are given in FIG. 11.

The analysis of the effects of APOTf on the parameter in question showed that, administered at 2.5 mg/kg, it is effective in reducing the extent of liver damage associated with the administration of ConA.

The invention claimed is:

1. A method of treating an autoimmune disease selected from the group consisting of multiple sclerosis, rheumatoid arthritis, inflammatory bowel syndromes and autoimmune hepatitis, said method comprising administering a therapeutically effective amount of Apo-transferrin (ApoTf) to a patient in need thereof for inducing a transition from the T-helper 1 immunological profile, characteristic of patients with pictures of immune hyperactivation, to the T-helper 2, typical of conditions of immune tolerance.

2. The method according to claim 1 wherein ApoTf is administered in a daily amount comprised between 1 and 10 mg/kg of body weight.

3. The method according to claim 1 wherein said autoimmune disease is multiple sclerosis and ApoTf is administered in a daily amount ≥2.5 mg/kg of body weight.

4. The method according to claim 1 wherein said autoimmune disease is rheumatoid arthritis and ApoTf is administered in a daily amount ≥1.0 mg/kg of body weight.

5. The method according to claim 1 wherein said autoimmune disease is inflammatory bowel syndromes and ApoTf is administered in a daily amount ≥5.0 mg/kg of body weight.

6. The method according to claim 1 wherein said autoimmune disease is autoimmune hepatitis and ApoTf is administered in a daily amount ≥2.5 mg/kg of body weight.

7. A method of treating autoimmune diseases, said method comprising administering, over a prolonged period of at least six times a week for at least six consecutive weeks, a therapeutically effective daily amount of Apo-transferrin (ApoTf) comprised between 2.5 and 10 mg/kg to a patient in need thereof for inducing a transition from the T-helper 1 immunological profile, characteristic of patients with pictures of immune hyperactivation, to the T-helper 2, typical of conditions of immune tolerance.

8. The method according to claim 7 wherein the prolonged administration is life-long.

9. The method according to claim 8 wherein said autoimmune diseases are selected from the group consisting of type 1 diabetes mellitus, multiple sclerosis, rheumatoid arthritis, inflammatory bowel syndromes and autoimmune hepatitis.

10. A method of treating type 1 diabetes mellitus comprising administering, over a prolonged period of time of at least six times a week for at least six consecutive weeks, a therapeutically effective daily amount of Apo-transferrin (ApoTf) comprised between 2.5 and 10 mg/kg to a patient in need thereof for inducing a transition from the T-helper 1 immunological profile, characteristic of patients with pictures of immune hyperactivation, to the T-helper 2, typical of conditions of immune tolerance.

11. The method according to claim 10 wherein the prolonged administration is life-long.

* * * * *